United States Patent [19]

Gentile et al.

[11] Patent Number: 5,252,312
[45] Date of Patent: Oct. 12, 1993

[54] PACKAGE EFFERVESCIBLE COMPOSITION

[75] Inventors: James L. Gentile, Orange; David R. Williams, Monroe; Alexander G. Ziemkiewicz, Shelton, all of Conn.

[73] Assignee: Chesebrough-Pond's USA Co., Division of Conopco, Inc., Greenwich, Conn.

[21] Appl. No.: 954,848

[22] Filed: Sep. 30, 1992

[51] Int. Cl.$^5$ ............... B65D 35/22; B65D 51/24; A61K 9/46; A61K 7/20
[52] U.S. Cl. ............... 424/44; 206/216; 206/219; 206/223; 206/568; 215/6; 215/228; 222/94; 222/129.4; 424/49; 424/53
[58] Field of Search ............ 206/216, 219, 223, 568; 215/6, 228; 222/94, 129.4; 424/44, 49, 53

[56] References Cited

U.S. PATENT DOCUMENTS

| | | | |
|---|---|---|---|
| 2,106,122 | 1/1938 | McGowan | 215/6 |
| 2,661,870 | 12/1953 | Huenergardt | 215/6 |
| 3,197,071 | 7/1965 | Kuster | 215/6 |
| 3,337,073 | 8/1967 | Angelo | 215/6 |
| 3,581,940 | 6/1971 | Cella | 222/94 |
| 3,705,661 | 12/1972 | Davis | 215/6 |
| 3,729,553 | 4/1973 | Gold et al. | 424/44 |
| 3,866,800 | 2/1975 | Schmitt | 222/94 |
| 4,592,489 | 6/1986 | Simon et al. | 222/94 |
| 4,687,663 | 8/1987 | Schaeffer | 424/52 |
| 4,837,007 | 6/1989 | Duckworth et al. | 424/52 |
| 4,884,703 | 12/1989 | O'Meara | 215/6 |
| 4,964,539 | 10/1990 | Mueller | 222/94 |
| 5,154,917 | 10/1992 | Ibrahim et al. | 424/7.1 |

FOREIGN PATENT DOCUMENTS 944506 4/1949 France.
92/04007 3/1992 PCT Int'l Appl.

Primary Examiner—Shep K. Rose
Attorney, Agent, or Firm—Milton L. Honig

[57] ABSTRACT

Disclosed is a packaged effervescible composition which generates fresh effervescence at the time of use. The composition comprises a first liquid component including hydrogen peroxide as a functional ingredient and a second liquid component including sodium bicarbonate as a functional ingredient. The package comprises a container for the components and a closure system comprising an inclined crown portion, at least two pouring spouts extending upwardly from the upper surface of the crown and a cover for securement to the crown portion, the cover being provided with depending plugs to close the closure. Preferably each pouring spout is provided with a vent opening which allows smaller through openings in the spouts. The through openings can thus be positioned closer together on the crown. This gives the advantage that the package can be used dispensing liquids into a small container such as a mouthwash cup with controlled pouring.

9 Claims, 4 Drawing Sheets

PACKAGE EFFERVESCIBLE COMPOSITION

TECHNICAL FIELD

This invention relates to a packaged effervescible composition. More particularly it relates to a packaged effervescible mouthwash composition which generates fresh effervescence at the time of use.

BACKGROUND OF THE INVENTION AND TECHNICAL PROBLEMS POSED BY THE PRIOR ART

Effervescent mouthwash compositions, especially carbonated mouthwash compositions, have been recognized as having desirable and advantageous properties. In U.S. Pat. No. 3,729,533 there is disclosed an effervescent composition packaged in a container having two compartments for storage of the components of the composition. Multi-compartment packaging is generally employed when it is necessary to keep the components of a composition separate until used to prevent premature reaction. In U.S. Pat. No. 3,729,553 the components are stored separately to help prevent premature mixing of the components and release of carbon dioxide. The components of U.S. Pat. No. 3,729,553 are said to be dispensed simultaneously and proportionately from the package.

In U.S. Pat. No. 4,687,663 there is described a semi-solid dental preparation having two components which are extruded and placed in contact on a toothbrush. When the brush is applied to teeth and gums, immediate mixing of the products takes place followed by the rapid evolution of oxygen and carbon dioxide. The oxygen is produced by exposure of hydrogen peroxide (the functional ingredient in one of the components) to catalase which is present in the mouth. The combination of oxygen and sodium bicarbonate (the functional ingredient in another one of the components) is believed to kill bacteria responsible for gum disease.

It is desirable to make a mouthwash based on a combination of hydrogen peroxide and sodium bicarbonate, however, there are problems with multi-compartment packaging intended for dispensing and storing liquid components. Firstly, there is a tendency for one or a mixture of the components to drain back into the compartments and spoil the contents. Secondly, the user of the package is given insufficient visual guidance on how to dispense the components from the package which can lead to unwanted premature mixing of the materials during pouring which leads to reaction of the hydrogen peroxide and sodium bicarbonate outside of the mouth with no beneficial oxygen evolution. Thirdly, known packaging for dispensing a multi-compartment composition is not adapted for uniform pouring of the components into small mouthed cups of the type typically used for mouthwash.

Thus, it would be desirable to provide a packaged effervescible composition with improved stability to premature reaction and improved dispensing capabilities.

SUMMARY OF THE INVENTION

A packaged effervescible mouthwash composition comprising a first liquid component including hydrogen peroxide as a functional ingredient and a second liquid component including sodium bicarbonate as a functional ingredient, said package comprising:

a container for the materials, said container having at least two discrete compartments each with an upper outlet end and a closure system for closing the compartments over said outlet end comprising:

an inclined crown portion having a peripheral skirt portion depending downwardly from an outer edge of the crown, said skirt portion being of sufficient size to engage a surface of the container in a fluid tight manner;

at least two pouring spouts extending upwardly from the upper surface of the crown, toward the lower edge thereof;

each pouring spout being provided with a through opening which extends from the upper end of the spout, through the crown and into a compartment; and a flat cover for securement to the crown portion toward an upper edge thereof, said cover being provided with at least two downwardly depending plugs, receivable in corresponding through openings of the crown so as to close the container.

The pouring spouts are preferably inclined so as to effect a pouring tip at the lower end of the spout. Preferably each pouring spout is provided with a vent opening located towards the upper edge of the crown which allows smaller through openings to be used than would be possible in their absence. Without the vent openings, the through openings must be large enough to allow air to enter the container during pouring in order to prevent "glugging" and uneven pouring. With vent openings, the through openings can be made smaller and therefore positioned closer together on the crown. This gives the advantage that the package can be used for simultaneously dispensing liquids from the package into a small container such as a mouthwash cup with controlled pouring.

The inclined crown of the closure and positioning of the pouring spouts towards the lower edge of the crown visually directs the user of the package to dispense liquid over the lower edge of crown only. This visual direction is enhanced by pouring spouts which are inclined to form a pouring tip. Pouring over the lower edge of the crown prevents premature mixing of the liquid streams. The spouts also aid the drain back of the components only into the compartment from which they were poured and helps prevent drain back of a mixture of the components into a compartment.

Other advantages and features of the present invention will become readily apparent from the following detailed description of the invention, from the claims, and from the accompanying drawings.

BRIEF DESCRIPTION OF THE DRAWINGS

In the accompanying drawings like numerals are employed to designate like parts.

DESCRIPTION OF THE PREFERRED EMBODIMENTS

For ease of description, the article of this invention is described in an upright position, and terms such as upper, lower, inclined etc. are used with reference to this position. It will be understood, however, that the article of this invention may be manufactured, stored, transported and sold in an orientation other than the position described.

Figure 1:
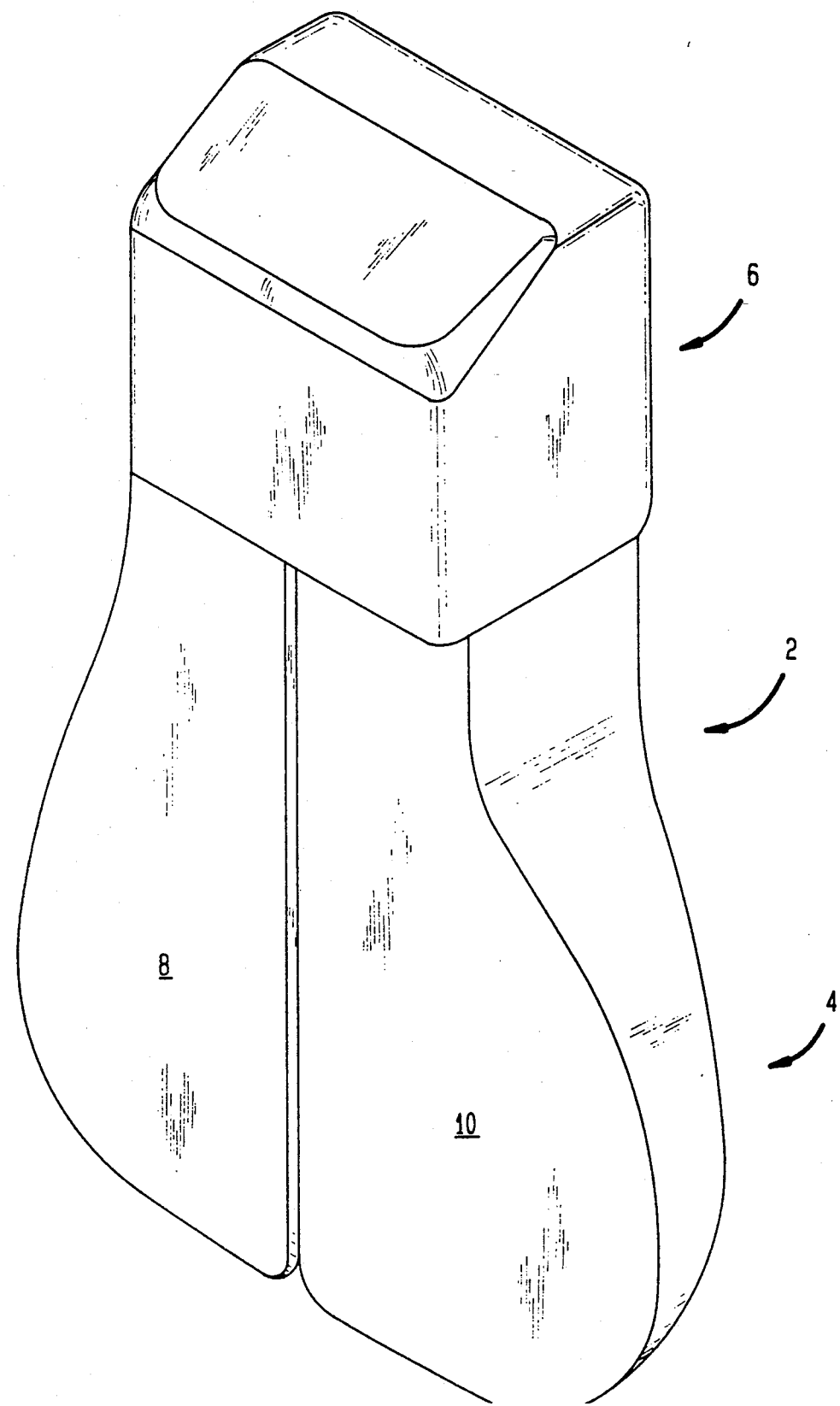
FIG. 1 is a perspective view of the packaged composition of the present invention shown with the cover in the closed position.

A first embodiment of a package in accordance with the teachings of the present invention is designated generally in FIG. 1 by the reference numeral 2. The package 2 comprises a container 4 and a closure 6. The container 4 comprises separate storage compartments 8, 10. Each compartment 8, 10 terminates upwardly with an outlet end 12, FIG. 3. The two-compartment container 4 can either be formed of two entirely separate compartments 8 and 10 which are held together by the closure system 6 as shown in FIG. 1 or can be formed by a dividing wall in the container.

The bottom of the container 4 may have any suitable configuration.

Figure 2:
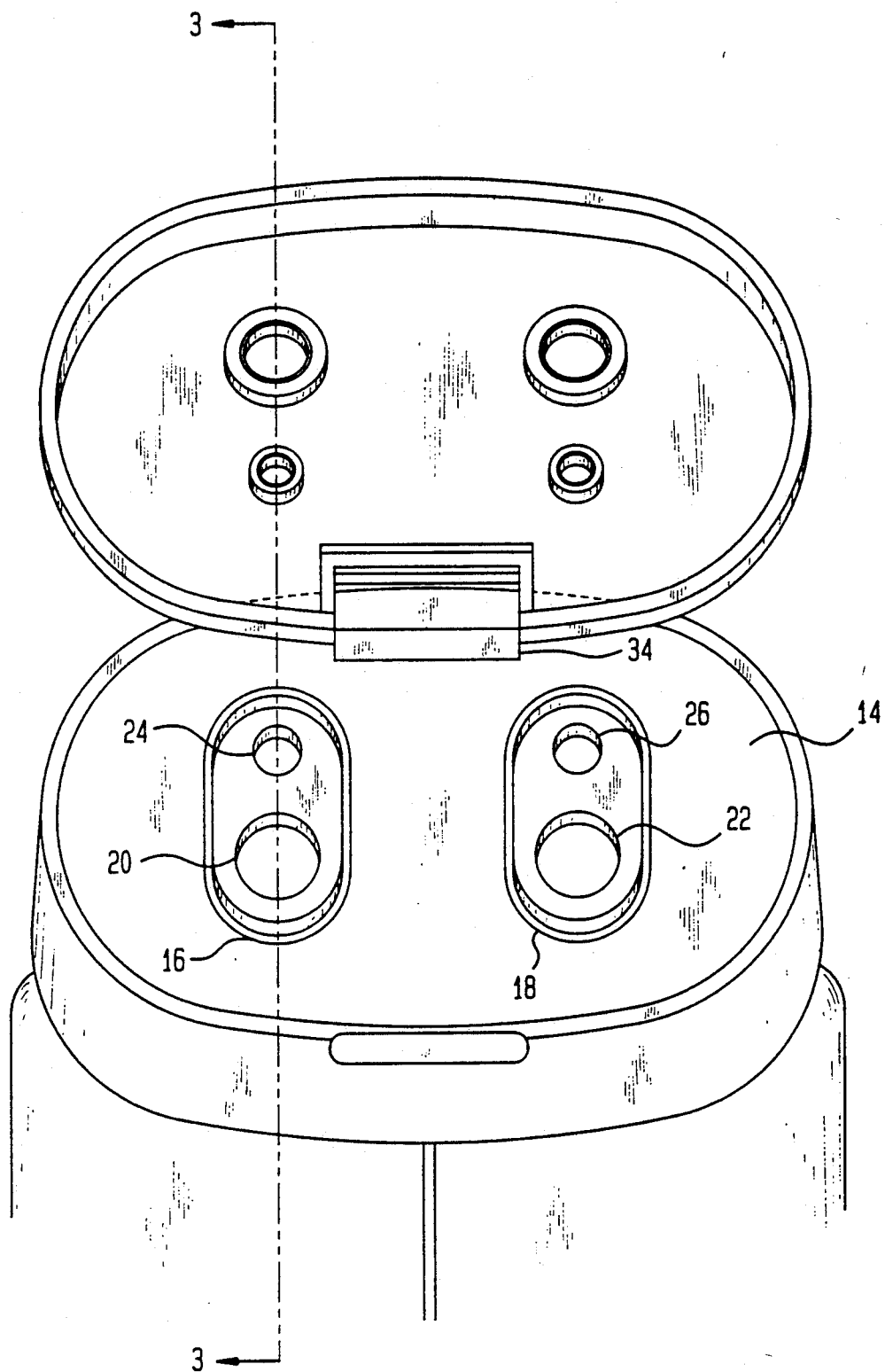
FIG. 2 is a top plan view of an alternative closure in the open position which may be mounted on a container.
Figure 3:
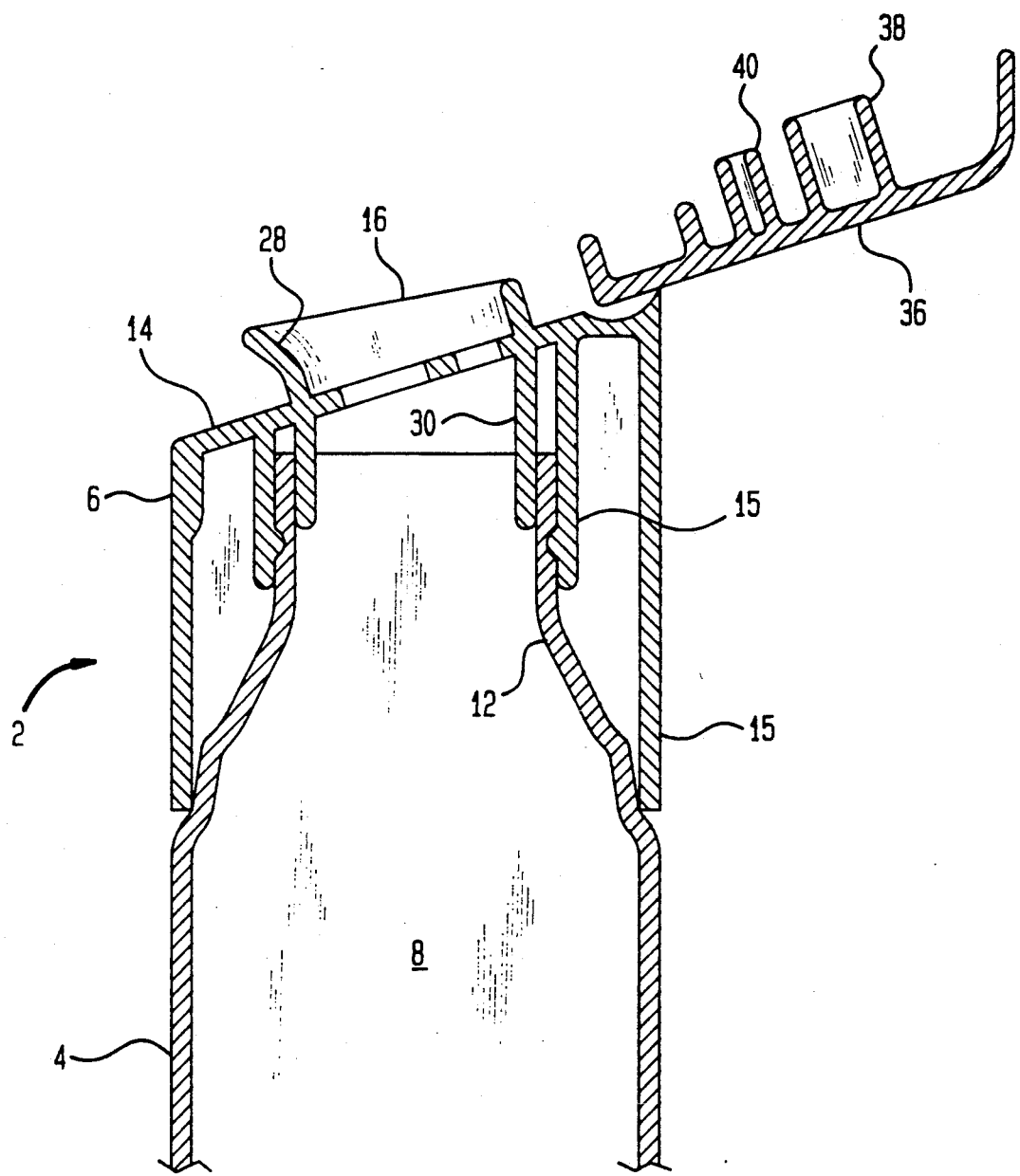
FIG. 3 is a fragmentary, cross-sectional view of the closure of FIG. 2 mounted on a container taken generally along the plane 3—3 of FIG. 2.

FIG. 2 and FIG. 3 show an alternative embodiment of the closure system 6 comprising an inclined crown portion 14 having one or more peripheral skirt portions 15 depending downwardly from an outer edge of the crown, to engage the outer surface of the container 4 in a fluid tight manner. To this end, the outer surface of the container 4 may be provided with an annular concave groove and the inner surface of the skirt 15 may be provided with an inwardly projecting, annular protuberance, bead or ring for engagement in the groove. This provides a conventional groove and bead snap-fit engagement which can be substituted with known equivalent engagements or seals. Two pouring spouts 16, 18 extend upwardly from the upper surface of the crown and are located toward the lower edge of the crown 14. The pouring spouts 16, 18 are each provided with a through opening 20, 22 which extends from the spout 16, 18, through the crown 14 and into a compartment 8, 10. Each spout is further provided with a vent opening 24, 26 which extends from the spout 16, 18, through the crown 14 and into a compartment 8, 10. Each spout 16, 18 is inclined to effect a pouring tip 28 shown in FIG. 3 for spout 16.

The inclined crown portion 14 has, in addition to the peripheral skirt portion 15, an inner skirt portion 30, as shown in FIG. 3, to engage the inner surface of the container 4 in a fluid tight manner.

The inclined crown portion 14 may have, towards its upper edge, a minor portion of reversed incline to that of the major portion of the crown 14 which portion can bear a hinge means for a flat cover as shown in FIG. 1. FIGS. 2 and 3 show inclined crown portion with a rotatable hinge 34 for a flat cover 36.

In the preferred embodiment illustrated in FIG. 1-3 the cover 36 is connected to the crown 14 via a snap-action hinge 34 that may be of a conventional molded plastic design. When the cover 36 is closed it is maintained in this position by the hinge. When the cover 36 is open it is maintained in this position to aid dispensing of the liquids with one hand. It will be appreciated that the cover 36 may be hingedly attached to the crown by many alternative means.

Flat cover 36 is provided with four depending plugs receivable in the through and vent openings 20, 22, 24, 26 of the spouts 16, 18. The plugs 38, 40 for through opening 20 and vent opening 24 of spout 16 are shown in FIG. 3. When the flat cover 36 is in the closed position as shown in FIG. 1, the plugs close the through and vent openings and seal the closure system and package. When the flat cover 36 is in the open position, liquids in compartments 8 and 10 are simultaneously dispensed by tilting the container 4 to a substantially horizontal position so that the liquids flow from the spouts 16, 18 over the lower edge of the crown 14. Each of the liquids flow by gravity from the container in a substantially uniform flow.

Preferably, the container 4 and closure 6 are each made of plastic. Conveniently, container 4 is formed by blow-molding, while closure 6 is injection molded. Most preferably container 4 is opaque.

In an alternative embodiment flat cover 36 is replaced by a removable cup which can also serve as a measuring cup and is retained on crown 14 by retaining lugs.

Figure 4:
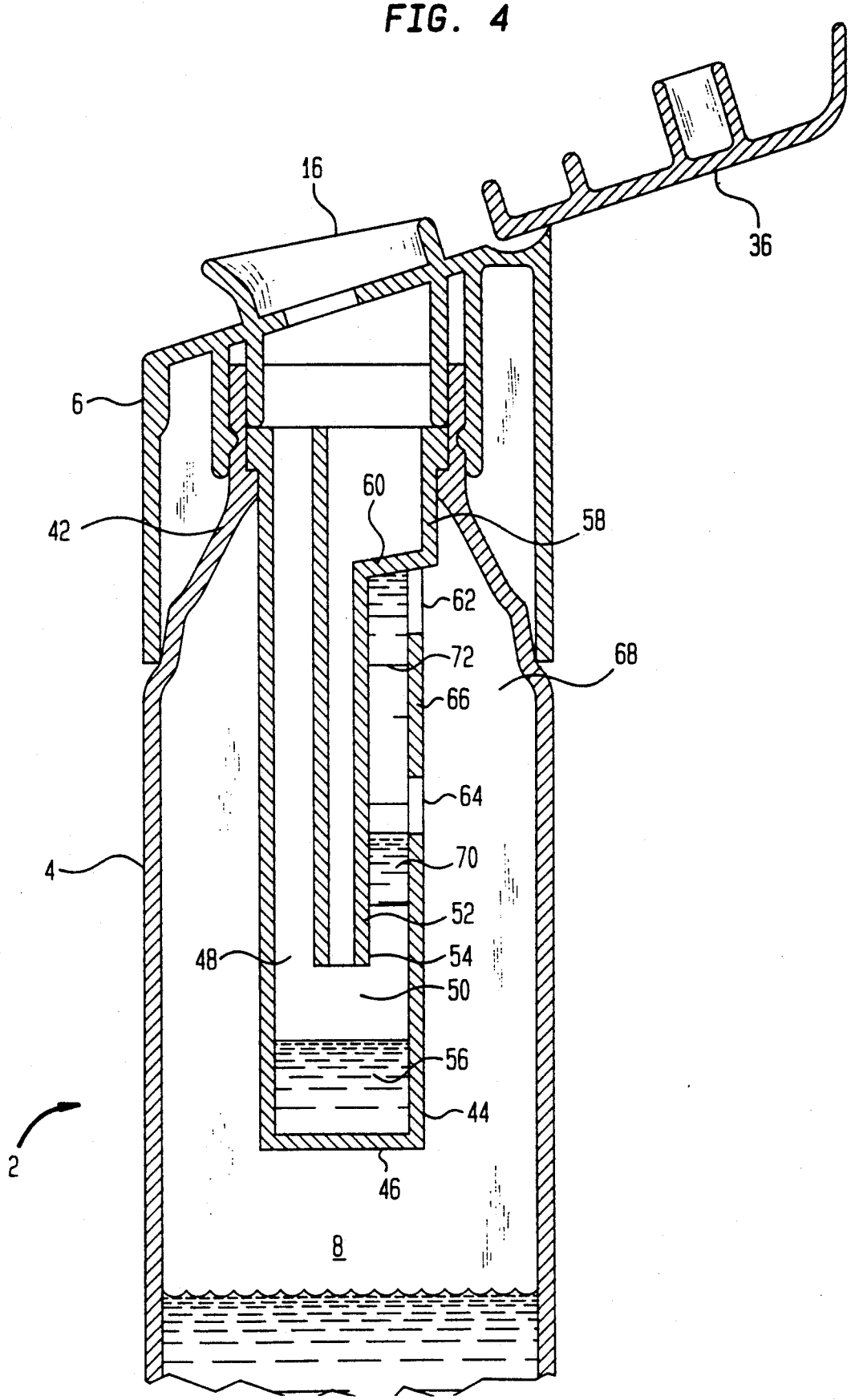
FIG. 4 is a fragmentary, cross-sectional view of the closure of FIG. 2 mounted on a container with a dosing device.

An additional embodiment of the present invention is illustrated in FIG. 4 and is substantially similar to the embodiments illustrated in FIGS. 1-3 except that each compartment 8, 10 is provided with a dosing device which aids the pouring of measured equal quantities of the liquids out of the package. FIG. 4 shows a dosing device installed in compartment 8 of the container 4 in the neck 42 thereof. The device projects into the interior of the container 4 while forming a seal with the container neck 42 by reason of the outer end of the dosing device fitting closely within the container neck 42.

The dosing device has at its inner end 44 a bottom 46. Two passages 48, 50 which are separated from one another by a partition wall 52, extend in the axial direction in the interior of the dosing device. The lower end 54 of the partition wall 52 is spaced from the bottom 46 to form a receptacle 56 which brings the two passages 48, 50 into communication with one another within the closed inner end 44 of the dosing device. The volume of the receptacle 56 is at least as large as the volume of liquid to be dispensed. The passage 48 acts as a through opening which is open at the spout 16 of the closure device 6. The other passage 50 is shut off from the outer end 58 of the dispensing device by transverse wall 60. Two apertures 62, 64 which are spaced apart in the axial direction of the passage 50, are provided in the outer wall 66 of the passage 50. The passage 50 communicates with the interior of the container through the two apertures 62 and 64, the outer wall 66 of the passage 50 being spaced from the neck of the container by a gap 68. Between the transverse wall 60 and the aperture 64 the passage 50 provides a measuring chamber, the volume of which is equal to the volume of liquid dispensed. The passage 50 also provides a collecting chamber between the aperture 64 and the end 54 of the partition wall, the volume of which is at least as great as half the maximum free liquid which occurs.

The mode of operation of the dosing device is as follows. When the container 4 is tilted, liquid flows from its interior through the gap 68 and through the aperture 62 into the passage 50, and at the same time the displaced air escapes from passage 50 through the aperture 64 into the interior of the bottle until the metering chamber 72 is filled with liquid to be dispensed as indicated by horizontal hatching in the drawing. When aperture 64 is so closed, no more air can enter the container. Only free liquid now flows into the collecting chamber 70 as shown by vertical hatching. As a result of the flow of free liquid the air in the interior of the bottle is at reduced pressure. If the container is returned to the vertical, the air at reduced pressure draws liquid out of the passage 50 through the aperture 64 into the interior of the container until the pressure is equalized. In consequence the measured quantity of liquid flows out of the metering chamber 72 into the receptacle 56. During the next tilting of the container 4 this quantity of liquid is poured out of the dosing device through the passage 48 and spout 16. In the course of this, the next metering operation takes place in the passage 50. While FIG. 4 shows the dosing device installed in one compartment of the container, each compartment of the container will normally contain a dosing device.

It will be readily observed from the foregoing detailed description and from the illustrated embodiments thereof that numerous variations and modifications may be effected without departing from the true spirit and scope of the principles of this invention.

The present invention thus provides packaged effervescible mouthwash composition comprising a first liquid component including hydrogen peroxide as a functional ingredient and a second liquid component including sodium bicarbonate as a functional ingredient. Preferably the first liquid component comprises from 0.5 to 5% by weight hydrogen peroxide, more preferably 1 to 5%. The second liquid component preferably comprises from 1 to 5% by weight sodium bicarbonate, more preferably 2 to 5%.

Other oral hygiene medicaments suitable for use in a mouthwash product may be used in the present invention, such as anti-caries agents, anti-calculus agents, anti-plaque agents, anti-microbial agents or the like.

Suitable anti-caries agents include fluoride ion sources, such as alkali metal fluorides, alkali metal monofluorophosphates, stannous fluoride, most preferably sodium fluoride. Fluoride ion sources may be used in an amount sufficient to provide from about 25 ppm to about 1000 ppm fluoride based on the total weight of the mouthwash.

Suitable anti-calculus agents include the linear molecular dehydrated polyphosphate salts, including alkali metal tripolyphosphates and pyrophosphates. Suitably, the polyphosphate anti-calculus agent may be used in an amount of up to about 5%, preferably from about 0.5 to about 2%, by weight, based on the total weight of the mouthwash.

The packaged effervescible mouthwash composition may include any suitable conventional ingredients. The ingredients commonly employed in mouthwash compositions include, for example, flavoring agents, anti-foam agents, alcohols, antimicrobial agents, sweetening agents, surface active agents, deodorizing agents, coloring agents, bactericidal agents, astringent agents and the like. Any number of the foregoing ingredients, as well as other conventional ingredients, may be present in the compositions of this invention.

The quantity of hydrogen peroxide and sodium bicarbonate employed in the liquid components will depend upon the desired quantity of oxygen to be made available from the two-liquid system, but preferably 4% by weight will be present in each compartment.

Generally, the mouthwash of the invention will comprise from about 45 to about 95%, by weight of water, based on the total weight of the mouthwash.

Conventional manufacturing techniques may be used to prepare the package and mouthwash of the invention.

The present invention is illustrated in terms of its preferred embodiments in the accompanying Examples. All parts and percentages referred to in this specification are by weight, based upon the total weight of the mouthwash, unless otherwise specified.

EXAMPLE 1

A hydrogen peroxide containing liquid and a sodium bicarbonate containing liquid were prepared by admixing the following ingredients:

| Ingredients | $H_2O_2$ Liquid | $NaHCO_3$ |
| --- | --- | --- |
| Deionized water | balance | balance |
| Ethanol | | 24 |
| Humectant (Polyol 2) | | 7 |
| Solubilizer (polysorbate) | | 0.4 |
| Flavor | | 0.4 |
| Sodium bicarbonate | | 2 |
| Hydrogen peroxide (35% sol.) | 4.285 | |
| Dye | 0.0025 | |
| Saccharin | | 0.065 |
| Sodium lauryl sulphate | | 0.6 |
| Phosphoric acid | 0.04 | |

Equal amounts of the liquids were added to compartments 8 and 10 of a package of the type shown in FIGS. 1 to 3. The liquids after being dispensed from the package combined to form an effervescent mouthwash.

We claim:

1. A packaged effervescible mouthwash composition comprising a first liquid component including hydrogen peroxide as a functional ingredient and a second liquid component including sodium bicarbonate as a functional ingredient, said package comprising:

a container for the materials, said container having at least two discrete compartments each with an upper outlet end and a closure system for closing the compartments over said outlet end comprising:

an inclined crown portion having a peripheral skirt portion depending downwardly from an outer edge of the crown, said skirt portion being of sufficient size to engage a surface of the container in a fluid tight manner;

at least two pouring spouts extending upwardly from the upper surface of the crown, toward the lower edge thereof;

each pouring spout being provided with a through opening which extends from the upper end of the spout, through the crown and into a compartment; and a flat cover for securement to the crown portion toward an upper edge thereof, said cover being provided with at least two downwardly depending plugs, receivable in corresponding through openings of the crown so as to close the container.

2. The mouthwash as claimed in claim 1 wherein the first liquid component comprises from 0.5 to 5% by weight of hydrogen peroxide.

3. The mouthwash as claimed in claim 1 wherein the second liquid component comprises from 1 to 5% by weight of sodium bicarbonate.

4. The mouthwash as claimed in claim 1 wherein the package is opaque.

5. The mouthwash as claimed in claim 1 wherein each compartment contains substantially the same quantity of liquid stored therein and the liquids are dispensed from said compartments in substantially the same amount.

6. The mouthwash as claimed in claim 1 wherein each pouring spout is provided with a vent opening which extends from the upper end of the spout, through the crown and into a compartment.

7. The mouthwash as claimed in claim 6 wherein the vent openings are positioned toward the upper edge of the crown.

8. The mouthwash as claimed in claim 1 wherein the pouring spouts are inclined to effect a pouring tip at the lower end of the spout.

9. The mouthwash as claimed in claim 1 wherein each compartment is provided with a dosing device.

* * * * *